United States Patent [19]

Williams

[11] Patent Number: Plant 6,819

[45] Date of Patent: May 30, 1989

[54] PEPPERMINT CANDY ROSE PLANT

[75] Inventor: J. Benjamin Williams, Silver Spring, Md.

[73] Assignee: NPI, Salt Lake City, Utah

[21] Appl. No.: 153,701

[22] Filed: Feb. 8, 1988

[51] Int. Cl.[4] ..... A01H 5/00
[52] U.S. Cl. ..... Plt./7
[58] Field of Search ..... Plt./7

*Primary Examiner*—Robert E. Bagwill

[57] ABSTRACT

A new and distinct variety of rose plant of the miniature rose class, which was originated by my crossing Rose Parade as seed parent and Easter Morning as pollen parent; characterized by well-formed delicate, creamy ivory-yellow blooms accented by a deep blush pink at the edge of petals and a deep yellow at the point of attachment. Individual flowers are borne singly and in clusters of three. The plant is vigorous and compact, producing abundant blooms which last well on the plant.

1 Drawing Sheet

The present invention relates to a new and distinct variety of rose plant of the miniature rose class named "Peppermint Candy," which was originated by my crossing as seed parent the rose known as "Rose Parade" (U.S. Plant Pat. No. 3,065) and the rose known as "Easter Morning" (U.S. Plant Pat. No. 2,177) as pollen parent.

Among the novel characteristics possessed by this new variety which distinguishes it from all other varieties of which I am aware are:

1. Exhibition type flowers of creamy ivory-yellow with a blush pink overlay on the outer edge of the distinctly recurled petals.
2. The well-formed, slightly cupped buds of this flower are a vivid pink, blending to a creamy ivory yellow, and finally to deep yellow at the heart. They open to 1–1¼", with the deep pink overlay becoming more prominent as flowers open. The reverse of the petals is a delicate ivory white.
3. This small plant produces its dainty blush pink and ivory flowers singly and in clusters of three.
4. This sturdy plant is vigorous, compact, and well-formed, growing 10 to 12" in height. The flowers are complemented by small to medium glossy, medium-green foliage.

Asexual reproduction by budding of the new variety as performed in Silver Spring, Md., and West Grove, Pa., shows that the foregoing and other distinguishing characteristics come true to form and are established and transmitted through succeeding propagation.

The new and improved rose variety which I have developed is a dainty ivory yellow washed with blush pink at the petal edges, and a delicate ivory on the reverse. The blush pink deepens as the flower fully opens and as it is exposed to the sun. The overall effect is enhanced by the deep yellow center and color holds well. Blooms come on a single stem and in clusters of three, complemented by small to medium, medium-green, glossy foliage. This vigorous plant produces abundant blooms which linger on the plant.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (R.H.S.C.C.) The terminology used in color description herein refers to plate numbers in the aforementioned color chart, e.g., "48-B" is plate 48-B of The Royal Horticultural Society Colour Chart.

Parentage: Seedling.
*Seed parent.*—"Rose Parade".
*Pollen parent.*—"Easter Morning".
Class: Miniature.

The following observations are made of specimens grown outdoors at Silver Spring, Md. and West Grove, Pa., during the months of June through September.

FLOWER

Blooming habit: Continuous.

A. Bud:
(1) *Size.*—Small.
(2) *Form.*—Full and slightly cupped.
(3) *Color.*—When sepals first divide: near 48-B. When petals begin to unfurl color is near 48-B on edge of inner petal with a blending downward to the base of attachment varying in color from 4-D to 4-C.
(4) *Sepals.*—Long and serrated, extending well beyond bud.
(5) *Peduncle.*—Length 4½ cm. Aspect — straight. Strength — heavy. Color — 146-C.

B. Bloom:
(1) *Size.*—1"–1¼".
(2) *Borne.*—Individually and in clusters of three.
(3) *Form.*—High-centered, with petals recurling as flower opens.
(4) *Petalage.*—20–22.
(5) *Color.*—During first two days. Center of flower — near 8-C blending to 8-D, with a wash of 61-D at edge of petals. Outer petals near 61-D. Base of petals: near 8-B. Reverse of petals — near 8-D.
(6) *Color change.*—General tonality from a distance is a delicate ivory yellow with deep blush pink overlay. Color is well maintained.

C. Petals:
(1) *Texture.*—Thick.

(2) *Appearance.*—Velvety.
(3) *Form.*—Somewhat diamond shaped, with prominent point at tip.
(4) *Arrangement.*—Regularly arranged shingle-like overlay.
(5) *Petaloids in center.*—Few.
(6) *Persistence.*—Drops off cleanly.
(7) *Fragrance.*—Light spicy fragrance.
(8) *Lasting quality.*—5–8 days on plant, 3–5 days as cut flower.

REPRODUCTIVE ORGANS

A. Stamens, anthers: Irregularly arranged around styles.
(1) *Color.*—Yellow-orange, near to 7-D.
B. Pollen: Color is greyish-orange near 163-C.
C. Styles: Thin, medium length.
D. Stigmas:
*Color.*—Orange-red — 138-D.
E. Hips: None observed.

PLANT

A. Form: Upright and compact.
B. Growth: Very vigorous.
*Height attained.*—10–12 in.
C. Foliage: Compound of 3 to 5 leaflets.
(1) *Size.*—Small to medium.
(2) *Quantity.*—Abundant.
(3) *Color.*—New foliage: upper side — 137-B, under side — 148-B. Old foliage: upper side — 137-C, under side — 148-C.
(4) *Shape.*—Oval, pointed.
(5) *Texture.*—Upper side — shiny, smooth. Under side — rough and dull.

(6) *Edge.*—Serrated.
(7) *Serration.*—5 per cm.
(8) *Leaf stem.*—Color — 147-B; under side — 147-C.
(9) *Stipules.*—Medium, slightly bearded.
D. Wood:
(1) *New wood.*—Color — 146-A. Bark — smooth.
(2) *Old wood.*—Color — 146-B. Bark — smooth.
E. Thorns:
(1) *Thorns.*—Quantity: on main stalks from base — ordinary; on laterals from stalk — very few. Form: flat base, pointed slightly downward. Length: medium. Color when young — 152-D. Position: irregular.
(2) *Prickles.*—Quantity: On main stalks — few; on laterals — none.
F. Plant's disease resistance:
(1) *Mildew.*—Very good.
(2) *Blackspot.*—Very good.
(3) *Rust.*—None observed.
G. Winter hardiness: Completely winter hardy.

I claim:

1. A new and distinct variety of rose plant of the miniature rose class, substantially as shown and described, characterized particularly as to novelty by well-formed delicate ivory yellow flowers highlighted by a deep blush pink overlay at the edge of petals and a deep yellow at the heart of the flower; small to medium, glossy, medium-green foliage growing on a vigorous, compact plant; vigorous habit of growth and hardiness; a light spicy fragrance; and its habit of producing blooms both singly and in clusters of three.

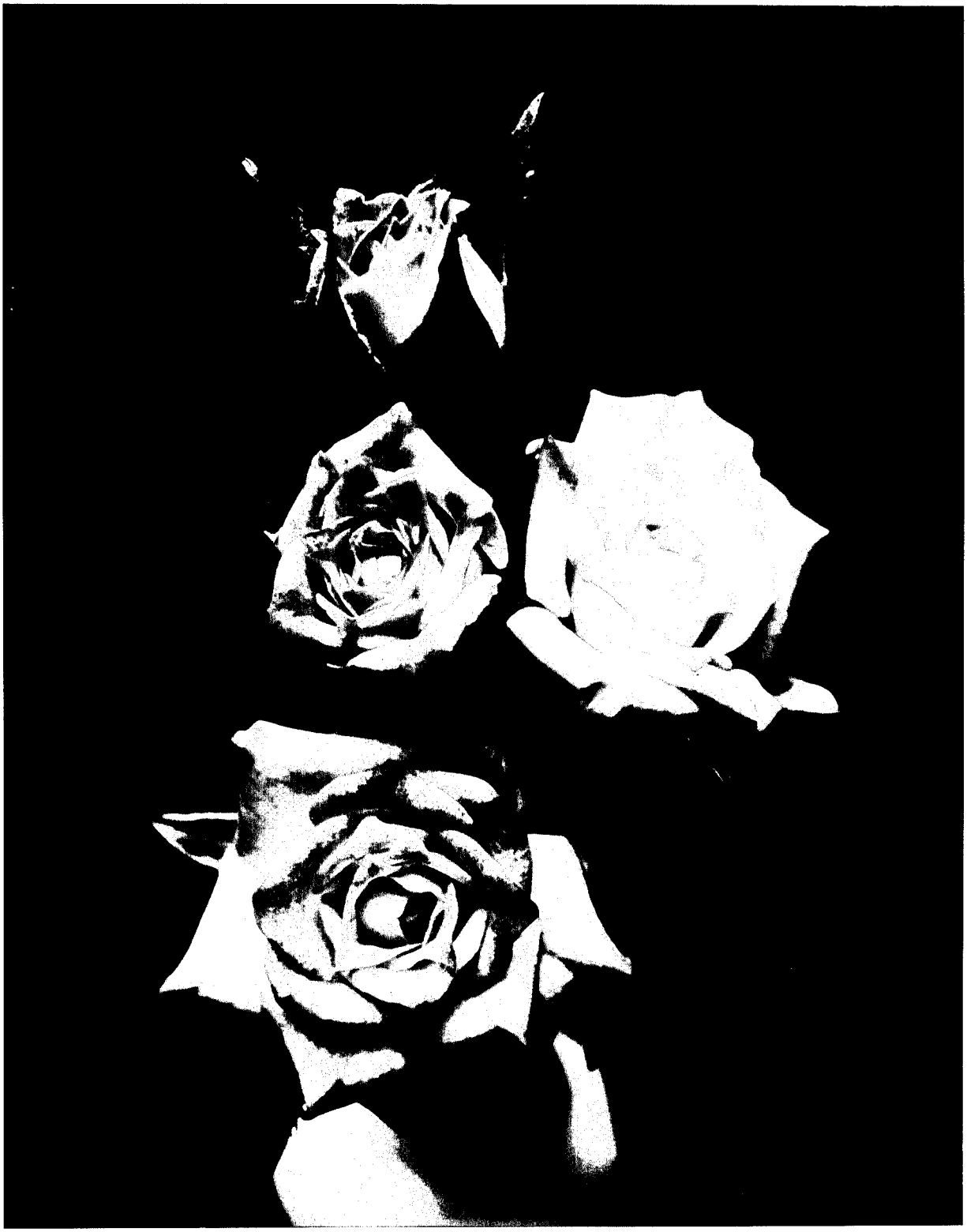

* * * * *